(12) United States Patent
Laghi

(10) Patent No.: US 8,197,555 B2
(45) Date of Patent: Jun. 12, 2012

(54) VALVE INTEGRATED PROSTHETIC EXPULSION PUMP

(75) Inventor: Aldo A. Laghi, Clearwater, FL (US)

(73) Assignee: Alps South, LLC, Saint Petersburg, FL (US)

( * ) Notice: Subject to any disclaimer, the term of this patent is extended or adjusted under 35 U.S.C. 154(b) by 239 days.

(21) Appl. No.: 12/755,567

(22) Filed: Apr. 7, 2010

(65) Prior Publication Data

US 2010/0262261 A1    Oct. 14, 2010

Related U.S. Application Data

(60) Provisional application No. 61/212,389, filed on Apr. 10, 2009.

(51) Int. Cl.
*A61F 2/80* (2006.01)
(52) U.S. Cl. .......................................... 623/34
(58) Field of Classification Search ............... 623/34
See application file for complete search history.

(56) References Cited

U.S. PATENT DOCUMENTS

| 6,063,125 A * | 5/2000 | Arbogast et al. ............... 623/34 |
| 6,979,355 B1 * | 12/2005 | Slemker ........................ 623/34 |
| 2008/0004716 A1 * | 1/2008 | Hoerner ........................ 623/34 |

* cited by examiner

*Primary Examiner* — Bruce E. Snow
*Assistant Examiner* — Melissa Hoban
(74) *Attorney, Agent, or Firm* — Shumaker, Loop & Kendrick, LLP; Ronald A. Christaldi

(57) ABSTRACT

An air expulsion pump for a prosthetic socket adapted to be worn on a residual limb of an amputee. The pump includes an elastomeric housing which fits snugly in a well defined in the lower end of the socket. The pump is easy to install by simply sliding it into the well. The pump has an upper surface commensurate with the inside surface of the socket in that both surface have the same radius of curvature. The pump includes an elastomeric spring member and two check valves that together with the elastomeric housing exert a continuous vacuum within the prosthetic socket. When donned by the user, the pump provides continuous total contact between the socket and the residual limb of the user as the user ambulates.

12 Claims, 2 Drawing Sheets

VALVE INTEGRATED PROSTHETIC EXPULSION PUMP

CROSS-REFERENCE TO RELATED APPLICATION

This application claims priority to provisional application No. 61/212,389 filed Apr. 10, 2009.

BACKGROUND OF THE INVENTION

The present invention relates generally to prosthetic devices and, more particularly, to a valve assembly for use with a prosthetic limb socket.

A prosthesis is often used to replace an amputated portion of a limb and to help restore the amputee's ability to use that limb. A prosthesis for a lower extremity amputation will often include an artificial foot connected to an upright assembly (pylon, tube or shaft) which is in turn connected to a custom fitted socket assembly.

Prior art prosthetic assemblies generally require an inner liner or sheath generally comprising a flexible, thermoplastic material conforming to the residual limb of the amputee, and a more rigid, thermoplastic outer socket which is attached to the upright assembly of the prosthetic assembly. The outer socket may or may not be used with the inner liner or sheath. The inner liner or sheath, when used, is usually donned by inverting and rolling it onto the residual limb. When used, the inner liner or sheath is typically designed to interface with and cushion the amputee's residual limb, to protect the amputee's residual limb from the interconnecting components which attach the outer socket to the upright assembly, and to provide an air-tight seal between the residual limb and the outer socket. The typical prior art prosthetic assembly included a relief valve mounted in the outer socket for the expulsion of air within the socket as it was donned. This type of prosthesis is typically held to the residual limb of the patient by suction formed between the inner liner or sheath or residual limb and the outer socket. To further maintain suction within the socket, a suspension sleeve is worn over the upper end of the socket and over the adjacent residual limb. Such suspension sleeves also hold the socket onto the residual limb.

One of the limitations encountered with this type of prosthetic assembly is that the weight of the prosthesis is carried mostly by the distal part of the residual limb. Another limitation is due to the location of the relief valve not being at the most distal point of the socket. As the residual limb with or without a liner or sheath is extended within the socket past the valve, the valve becomes blocked by the residual limb and thus fails to expel all of the air from within the socket.

Throughout the development of these type of prostheses, it was found that total contact was essential between the residual limb and the socket to attain an even weight distribution of the patient and to distribute the suspension of the prosthesis over the whole surface of the residual limb.

Furthermore, it is well known that when an amputee dons a prosthesis and begins taking the pressures of transmitting the weight of the body through the surface area of the residual limb to the bone, there is increased pressure on the residual limb which causes the eventual loss of fluids within the residual limb. This loss of fluids causes the volume of the residual limb to decrease during the day. It varies from amputee to amputee, but it is a constant among all amputees and the more "fleshy" and the softer the residual limb, the more volume fluctuation there will be. The greater the weight and the smaller the surface area, the greater the pressures will be and the more "swings" there will be in fluids. In the past, the amputee had to compensate for this volume decrease by removing the artificial limb and donning additional stump socks to make up for the decreased residual limb volume. The volumetric dimensions of the residual limb will change within a very short period of time due to fluid retention or fluid loss.

Because of such pressures on the residual limb resulting in volume changes thereof, pistoning during ambulation of the residual limb within the socket occurs since the prosthesis does not fit well at all times.

One typical system designed to create such suction and compensate for varying residual limb volume is disclosed in U.S. Pat. No. 6,761,742 to Caspers. The Caspers patent discloses various embodiments of suction systems associated with the type of prosthesis discussed above. In one embodiment, Caspers discloses a vacuum pump attached to the upright assembly which includes a mechanical or motor-driven pump. The pump is fluidically connected to the interface between the liner and socket via conduits, thus creating a vacuum within the prosthetic socket to draw the liner into close contact with the socket. In another embodiment, Caspers discloses a weight-actuated vacuum pump mechanically actuated by downward force exerted on the pump during ambulation of the amputee. This pump is also mounted in the upright assembly and is fluidically connected to the interface between the liner and socket via a passageway extending through the upright assembly itself.

Another typical system is disclosed in U.S. Pat. No. 6,287,345 to Slemker et al. which includes a prosthetic socket having a distal extension. Mounted within the distal extension is a valving system for relieving air from within the socket as the amputee donns the prosthesis socket. Although this valving system operates efficiently, the manufacture and assembly thereof is quite complicated since it includes several intricately molded parts some of which are made of metal. Furthermore, the valving system is attached to the prosthetic socket with screws.

Thus, from the above examples of the prior art systems, some of the drawbacks are noise and weight related to the use of metal components in the pump body, packaging limitations due to the geometry of the pumps, which affect the cosmetic appearance of the prosthesis, the need for batteries or other power sources, and the need for pistons and cylinders to pump air out of the socket.

The present invention is a novel and unique design to overcome all the limitations highlighted above of the current prior art systems.

SUMMARY OF THE INVENTION

It is an object of the present invention to provide an air expulsion pumping system for a prosthetic socket that is easy to manufacture.

It is a further object of the present invention to provide an air expulsion pumping system for a prosthetic socket that is easy to install in a prosthetic socket without the use of any physical fasteners.

It is a further object of the present invention to provide an air expulsion pumping system for a prosthetic socket that is easily replaceable without destroying the prosthetic socket.

It is an object of the present invention to provide an air expulsion pumping system for a prosthetic socket that is manufactured with few moving parts.

The present invention is an air expulsion pumping system for a prosthetic socket. The prosthetic socket made of a substantially rigid material and an open proximal end and an opposite distal end and adapted to receive the residual limb of an amputee. The prosthetic socket distal end formed with an extension having inside surfaces defining a well and outside surfaces adapted to be connected to an upright assembly of a prosthetic assembly. Mounted within the well is an air expulsion pump having a valve housing made of elastomeric components having outer surfaces complementally configured to the inside surfaces of the well such that the pump housing fits in sealing relationship within the distal extension.

In the preferred embodiment of the present invention, the pump housing comprises two elastomeric components with one slidingly received within the other. The pump housing further includes internal surfaces defining an internal air reservoir surrounding an internal elastomeric spring member. The elastomeric spring member having upper and lower surfaces in sealing engagement with the internal surfaces of the pump housing. The air expulsion pump includes a central passageway extending through the pump housing, internal elastomeric spring member and distal extension of the prosthetic socket. The elastomeric spring member having at least one lateral passageway extending from the central passageway to the air reservoir. Within the central passageway are first and second one-way valves; the first one-way valve being located upstream of the at least one lateral passageway, and the second one-way valve being located downstream of the at least one lateral passageway.

In the above preferred embodiment, the distal end of prosthetic socket has a curved interior surface from which the inside surfaces of the well extend. The pump housing, when fitted within the well, having an upper surface congruent with the curvature of the interior surface of the socket to define a smooth interior curvature at the distal end of the prosthetic socket. When the prosthetic socket is used with an elastomeric liner or sheath, the smooth interior curvature at the distal end of the prosthetic socket together with the liner or sheath provides a comfortable fit of the residual limb within the socket. The elastomeric spring member is selected based on the degree of vacuum deemed appropriate for each individual patient. As the patient donns the prosthesis, air will be forced out of the socket through the central passageway. After the prosthetic is donned and the patient ambulates, any air remaining between the residual limb and socket, or between the liner or sheath and socket, will be suctioned out through the central passageway via the action of the expulsion pump providing continuous total contact between the residual limb and the socket.

DETAILED DESCRIPTION OF THE INVENTION

Figure 1:
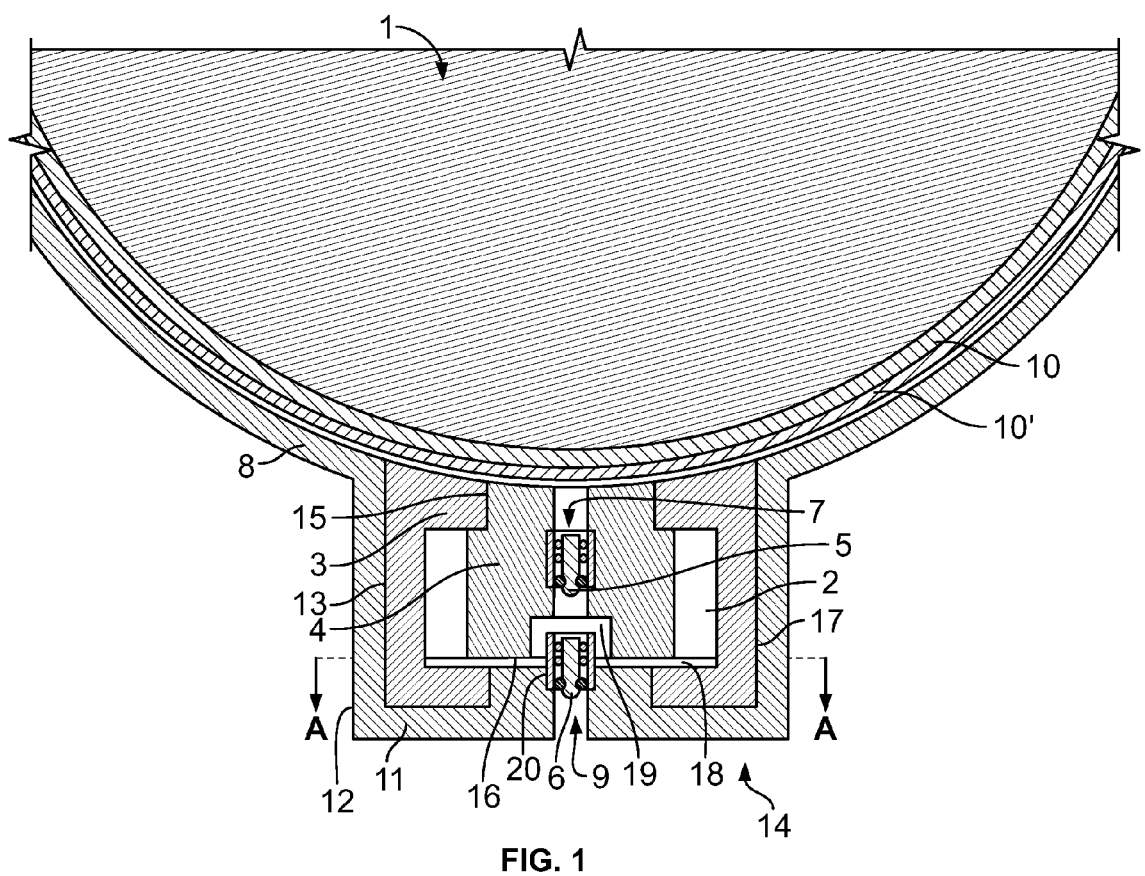
FIG. 1 is a cross-sectional view of the air expulsion pump mounted in the distal end of a prosthetic socket of the present invention.
Figure 2:
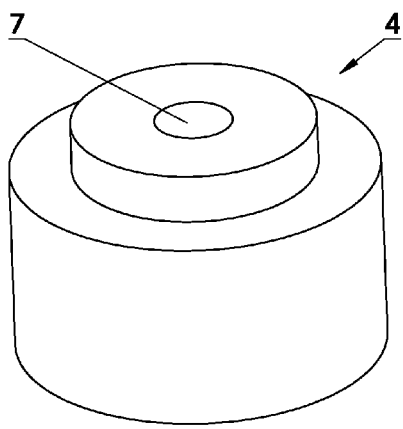
FIG. 2 is a perspective view of the elastic spring member of the air expulsion pump.
Figure 3:
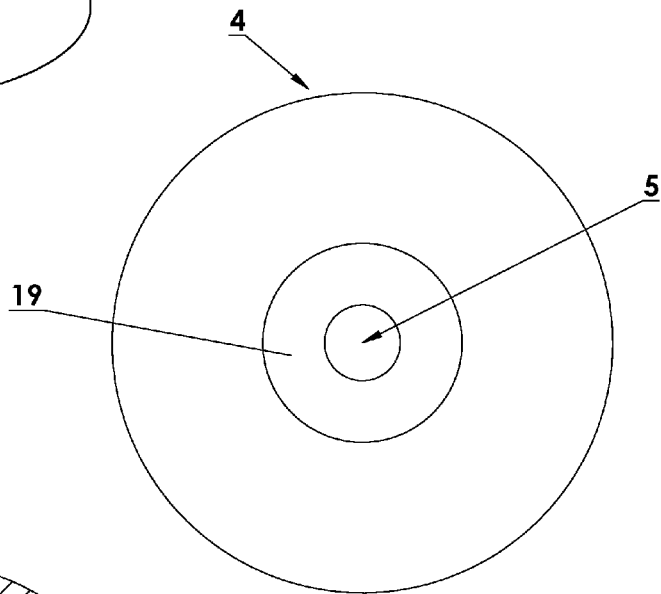
FIG. 3 is a bottom view of the elastic spring member of FIG. 2.
Figure 4:
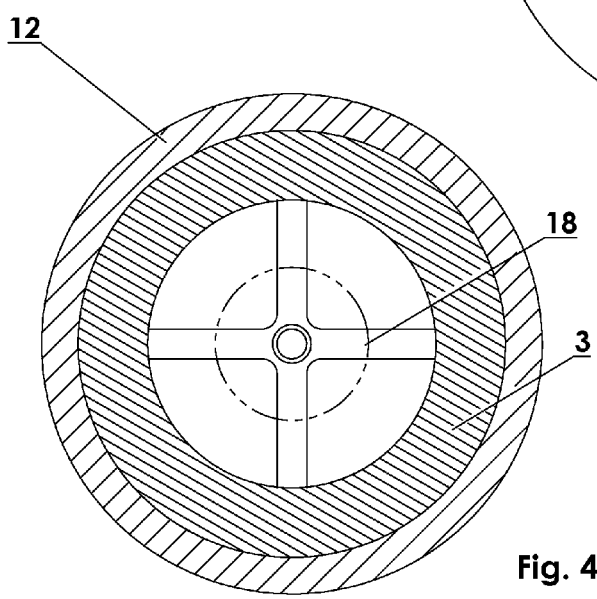
FIG. 4 is a cross-sectional view of the air expulsion member taken along the lines A-A.

As shown in FIG. 1, a residual limb 1 of a patient is fitted with an elastomeric liner or sheath 10 having an exterior fabric surface 10' and inserted into a prosthetic socket 8. The air expulsion pumping system 14 is shown mounted within the distal end of the prosthetic socket. The prosthetic socket 8 may be constructed of a substantially rigid material such as polyester or acrylic resin or thermoset plastics including polypropylene and polyethylene, or any other appropriate materials. One example illustrating the manufacture of a prior art prosthetic socket is disclosed in U.S. Pat. No. 5,571,208 to Caspers, which is incorporated herein by reference. It is noted that this is the typical prosthetic system having an air expulsion valve 112 that the present invention improves upon. The socket of the present invention could be worn with a liner donned over the residual limb of the patient such as liner 90 in the system disclosed in U.S. Pat. No. 5,571,208, or with a liner 10 having a fabric 10' coated on the exterior surface thereof such as the Single Socket Gel Liner disclosed by Silipos in O&P Business News dated Jan. 1, 1995 on page 16. Prosthetic socket 8, at its distal end, includes extension 11 having bottom and side walls with outside surfaces 12 shaped to provide a complemental fit to an upright assembly (not shown). The shape of the outside surface 12 could be of any configuration, preferably cylindrical-shaped, that would be complementally configured to the shape of a top end of an upright assembly. The extension 11 is to be fastened in any conventional manner, i.e., by bonding or mechanical fasteners, to the top end of an upright assembly. The interior surfaces 13 of the extension 11 define a well for air expulsion pump system 14. The shape of the interior surfaces 13 could also be of any configuration, preferably cylindrical-shaped. The air expulsion pump 14 includes a pump housing body 3 having top, side and bottom walls sized to fit within the well. Within the pump housing body 3 is mounted an elastic spring member 4. As best illustrated in FIGS. 1 and 2, the elastic spring member 4 includes a central passageway 7 therethrough defining a central air inlet and expanded air outlet 19. The pump housing body 3 and elastic spring member 4 are made of an elastomer and are sealingly joined at interfaces 15 and 16. The pump housing body 3 defines an outer surface 17 that provides a complemental snug fit with the interior surfaces 13 of the extension 11. Defined between the pump housing body 3 and the elastic spring member 4 is annular air reservoir 2. As best illustrated in FIGS. 1 and 4, the lower wall of the pump housing body 3 includes upwardly extending channels 18. The top wall of the pump housing body 3 includes an upper surface congruent with the curvature of the interior surface of the socket. The upper surface of the elastic spring member 4 is also congruent with the curvature of the interior surface of the socket. The upper surfaces of the pump housing body 3 and elastic spring member 4 together are commensurate with the interior surface of the socket. In other words, they each lie in the same spherical plane and have the same radius of curvature as the interior surface of the socket, thereby defining a smooth interior spherical surface at the distal end of the prosthetic socket. The elastic spring member 4 is made of an elastomer material selected to provide a prescribed degree of vacuum within the socket as deemed appropriate for each patient and would be determined based on the size and weight of the patient. The bottom wall of the pump housing body 3 includes a central passageway 20 aligned with the central passageway 7. The bottom wall of the extension 11 includes a central air outlet 9 aligned with the central passageway 7. Channels 18 define lateral air passages extending between the central passageway outlet 19 and air reservoir 2. A first one-way valve 5 is disposed in the central passageway 7 upstream of the lateral air passages 18. A second one-way valve 6 is disposed in the central passageway 20 downstream of the lateral air passages 18. These one-way valves can be of any conventional type one-way valve such as spring biased popped-type valves or duck-bill valves.

The operation of the present invention will now be described. As the patient donns the socket, air will be force out of the inlet and outlet valves through the central passageway 20. After the socket is almost full donned and as the patient begins to ambulate, with the initial downward step, the downward force of the residual limb within the socket will force any remnant air within the lower section of the socket out through central passageway 7 through first one-way valve 5, into the air reservoir 2 and out through the outlet valve 6 while simultaneously compressing the elastic spring member 4 downwardly. As the patient lifts his limb off the ground for the next step, the elastomeric spring member 4 expands causing valve 6 to close and valve 5 to open and draw more air from within the socket into the reservoir 2. As the patient takes the next step, causing elastomeric spring member 4 to compress again, the air pressure in air reservoir 2 causes valve 6 to open while maintaining valve 5 closed thereby relieving air from within air reservoir 2 to be vented through outlet 9. The cycle is repeated as the patient ambulates creating a continuous evacuation of air from within the socket as the patient ambulates during both a down step as well as an up step, thereby maintaining continuous total contact between the residual limb and the socket

I claim:

1. A prosthesis for providing total contact between a residual limb of a patient and the interior of a prosthetic socket as the patient ambulates comprising:

a prosthetic socket having an open proximal end and a distal closed end except for a central opening and configured to receive a residual limb of an amputee in sealing relationship thereto;

said socket having a distal concave-shaped interior surface;

an extension depending from said distal end of said socket around said central opening; said extension having side walls and a bottom wall, said walls defining interior side surfaces aligned with said central opening of said socket, a bottom interior surface and exterior surfaces; said exterior surfaces adapted to be attached to an upright assembly acting as an artificial limb; said bottom wall having a central air passageway extending therethrough defining an air outlet; said interior side surfaces and said interior bottom surface defining a well;

an air expulsion pump mounted in said well;

said air expulsion pump comprising an elastomeric housing, an elastomeric spring member, a first one-way valve preventing backflow and a second one-way valve preventing backflow;

said elastomeric housing and said elastomeric spring member having exterior surfaces in sealing relation with said interior side surfaces and said interior bottom surface of said well;

said elastomeric housing and said elastomeric spring member having concave-shaped exterior surfaces disposed within said central opening of said socket;

said concave-shaped exterior surface of said elastomeric pump housing, said concave-shaped exterior surface of said elastomeric spring member and said socket distal concave-shaped interior surface each lying in a common concave-shaped plane, said concave-shaped exterior surface of said elastomeric spring member defining an air inlet;

an air flow passageway extending from said air inlet through said elastomeric spring member and said central air passageway thereby providing air flow from said socket to said air outlet; and said first and second one-way valves disposed in said air passageway such that, as the patient ambulates, air is continuously drawn from the socket through said air inlet, through said first one-way valve, through said air passageway and then through said second one-way valve to said outlet, thereby providing total contact between the residual limb of the patient and the interior of the socket.

2. A prosthesis as claimed in claim 1, further comprising an air reservoir formed by said elastomeric pump housing and said elastomeric spring member between said first and second one-way valve members, wherein, as said patient steps down, said elastomeric pump housing and said elastomeric spring member compress to force air from said air reservoir, through said second one-way valve and out through said air outlet; and wherein, as said patient uplifts the residual limb, said elastomeric pump housing and said elastomeric spring member expand drawing air from said socket through said first one-way valve and into said air reservoir, whereby as said patient ambulates, the cycle is repeated to provide a continuous suctioning of air from said socket.

3. A prosthesis as claimed in claim 1, wherein said central opening in said socket and said interior surface of said extension are substantially cylindrical-shaped.

4. A prosthesis as claimed in claim 3, further comprising said pump housing having top, side and bottom walls; said pump housing side and bottom walls having exterior surfaces fitted snugly within said well in sealing relation thereto.

5. A prosthesis as claimed in claim 4, further comprising said elastomeric spring member having exterior side, top and bottom surfaces; said pump housing having interior side, top and bottom surfaces; and said elastomeric spring member exterior top and bottom surfaces are in sealing engagement with said pump housing top and bottom interior surfaces, respectively.

6. The prosthesis as claimed in claim 5, wherein said elastomeric spring member exterior top surface defining an annular ledge, and said upper wall of said pump housing includes an inwardly extending flange defining an interior top surface in sealingly engagement with said ledge.

7. A prosthesis as claimed in claim 5, further comprising said pump housing interior surfaces together with said elastomeric spring member exterior surfaces defining an air reservoir therebetween;

said air flow passageway extending from said air inlet, through said elastomeric spring member, through said air reservoir, through said central air passageway in said pump housing bottom wall and through said air outlet;

said first one-way valve disposed in said air passageway between said air reservoir and said air inlet; and said second one-way valve disposed in said air passageway between said air reservoir and said air outlet;

whereby said first and second one-way valves provide one-way flow from said air inlet to said air outlet.

8. A prosthesis as claimed in claim 7, further comprising said elastomeric spring member bottom surface together with said pump housing interior bottom surface defining lateral air channels fluidically communicating said central air passageway with said air reservoir.

9. The prosthesis as claimed in claim 1, wherein said extension is integrally molded with said socket.

10. The prosthesis as claimed in claim 1, wherein said elastomeric spring member includes an annular ledge, and said upper wall of said elastomeric pump housing includes an inwardly extending flange in sealing engagement with said ledge.

11. The prosthesis as claimed in claim 1, wherein said first one-way valve is disposed in said air flow passageway extending through said elastomeric spring member, and said second one-way valve is disposed in said central air passageway extending through said bottom wall of said pump housing.

12. A prosthesis for providing total contact between a residual limb of a patient and the interior of a prosthetic socket as the patient ambulates comprising:

- a prosthetic socket having an open proximal end and a distal closed end except for a central circular opening and configured to receive a residual limb of an amputee in sealing relationship thereto;
- said socket having a distal spherical-shaped interior surface;
- an extension having an open first end, an opposite second end, a side wall and a bottom wall extending across said opposite second end; said first end integrally connected to said distal end of said socket around said central circular opening; said extension having a cylindrical interior side surface aligned with said central circular opening and an exterior surface; said exterior surface adapted to be attached to an upright assembly acting as an artificial limb; said bottom wall having an interior lower surface and a central air passageway extending therethrough defining an air outlet; said cylindrical interior side surface and said interior lower surface defining a cylindrical-shaped well;
- an air expulsion pump comprising a cylindrical-shaped pump housing having a spring member mounted therein; said pump housing and spring member made of elastomeric material;
- said pump housing having top, side and bottom walls; said pump housing side and bottom walls having exterior surfaces fitted snugly within said well in sealing relation thereto;
- said elastomeric spring member having exterior side, top and bottom surfaces;
- said elastomeric pump housing having interior side, top and bottom surfaces;
- said elastomeric spring member top and bottom exterior surfaces are in sealing engagement with said elastomeric pump housing top and bottom interior surfaces, respectively;
- said elastomeric pump housing top wall having an exterior top surface surrounding said elastomeric spring member exterior top surface;
- said socket spherical-shaped distal surface, said elastomeric pump housing exterior top surface and said elastomeric spring member top surface all lying in the same spherical-shaped plane, thereby defining a smooth interior spherical-shaped surface at the distal end of said socket;
- said elastomeric pump housing interior side surfaces together with said elastomeric spring member exterior side surfaces defining an air reservoir therebetween;
- a central air passageway extending through said elastic spring member, through said pump housing bottom wall and aligned with said air outlet;
- said elastomeric spring member bottom surface together with said elastomeric pump housing interior bottom surface defining lateral air channels fluidically communicating said central air passageway with said air reservoir;
- a first one-way valve disposed in said central air passageway downstream of said air channels and adapted to provide one-way flow from said air reservoir to said air outlet;
- a second one-way valve disposed in said central air passageway upstream of said air channels and adapted to provide one-way flow from said socket to said air reservoir;
- whereby, as a patient ambulates, said elastomeric spring member together with said elastomeric pump housing is compressed during step down and expands during leg lift wherein air is constantly suctioned from said socket to said air reservoir during a leg lift and from said air reservoir to said air outlet during a down step, thus maintaining total contact between the residual limb and the interior surface of the socket.

* * * * *

UNITED STATES PATENT AND TRADEMARK OFFICE
CERTIFICATE OF CORRECTION

| | |
|---|---|
| PATENT NO. | : 8,197,555 B2 |
| APPLICATION NO. | : 12/755567 |
| DATED | : June 12, 2012 |
| INVENTOR(S) | : Aldo A. Laghi |

It is certified that error appears in the above-identified patent and that said Letters Patent is hereby corrected as shown below:

Title Page, item (74);
The name "Ronald A. Christaldi" on the face of the above patent should be deleted and Henry J. Recla should be added as the agent of record.

Signed and Sealed this
Thirty-first Day of July, 2012

David J. Kappos
*Director of the United States Patent and Trademark Office*